United States Patent [19]

Kabanov et al.

[11] 4,187,197

[45] Feb. 5, 1980

[54] CATALYST FOR THE DIMERIZATION OF OLEFINS

[76] Inventors: Viktor A. Kabanov, Lomonosovsky prospect, 14, kv. 108; Marina A. Martynova, ulitsa Stasovoi, 4, kv. 34; Stanislav K. Pluzhnov, pereulok Yazykovsky, 5, kv. 104; Vladimir I. Smetanjuk, ulitsa Stasovoi, 4, kv. 34, all of Moscow, U.S.S.R.

[21] Appl. No.: 895,341

[22] Filed: Apr. 11, 1978

Related U.S. Application Data

[62] Division of Ser. No. 779,263, Mar. 18, 1977, Pat. No. 4,118,432.

[51] Int. Cl.$^2$ ............ B01J 31/22; B01J 31/24
[52] U.S. Cl. ............ 252/431 P; 252/429 B; 252/431 C
[58] Field of Search ............ 260/683, 150; 252/429 B, 431 C, 431 P

[56] References Cited

U.S. PATENT DOCUMENTS

| | | | |
|---|---|---|---|
| 2,956,994 | 10/1960 | Peterlein | 252/429 B X |
| 3,652,678 | 3/1972 | Allum et al. | 252/431 P X |
| 3,872,026 | 3/1975 | Dunn | 252/431 P X |
| 4,000,211 | 12/1976 | Smith et al. | 252/429 B X |

*Primary Examiner*—Patrick Garvin
*Attorney, Agent, or Firm*—Lackenbach, Lilling & Siegel

[57] ABSTRACT

A method and composition for dimerization of olefins containing 2 to 4 carbon atoms, wherein at least one of said olefins is mixed, in a medium of hydrocarbon or halogenated hydrocarbon solvents at a temperature ranging from 0° to 100° C. under a pressure of from 1 to 40 atm with a two-component catalyst consisting of:

(1) a complex of a nickel salt with a tertiary phosphine or tertiary phosphite;
(2) an organoaluminum compound comprising a natural or synthetic carbochain rubber, swellable in said solvents, containing 2 to 50 mol. % of AlRX units, wherein R is an alkyl with at most 8 carbon atoms, X is a halogen; atomic ratio Al/Ni being varied within the range of from 1 to 100.

The catalyst employed in the method according to the present invention features high stability (retaining its original activity for a long time); it is not crushed and can be readily regenerated. The catalyst demonstrates high selectivity: a content of butene-1 in a mixture of butenes obtained from dimerization of ethylene is as high as 80%; content of methylpentenes in a dimerizate resulting from dimerization of propylene is as high as 90 to 95%.

3 Claims, No Drawings

CATALYST FOR THE DIMERIZATION OF OLEFINS

This is a division of application Ser. No. 779,263 filed Mar. 18, 1977, now U.S. Pat. No. 4,118,432.

The present invention relates to petrochemistry and, more specifically, to methods for dimerization of olefins. The resulting olefins are useful as monomers and comonomers in the production of polyolefins, as starting feedstock for the production of monomers in the manufacture of synthetic rubber and the like.

Known in the art are processes for dimerization of olefins by mixing thereof with different homogeneous or heterogeneous catalysts.

Known as most efficient is a process for dimerization of olefins contemplating the use of a two-component catalyst consisting of (1) an organoaluminum compound of the formula $R_nAlX_{3-n}$ where R is an alkyl, X is a halogen, n is 1 or 2; (2) a complex of a nickel salt of an organic or inorganic acid with tertiary phosphine or tertiary phosphite, the atomic ratio Al/Ni being varied within the range of from 1:1 to 100:1. Dimerization is conducted in a medium of hydrocarbon or halogenated hydrocarbon solvents at a temperature ranging from 0° to 100° C. under a pressure of from 1 to 40 atm.

This catalyst makes it possible to perform dimerization of olefins under mild conditions at a high rate. However, said prior art process making use of the above-described catalyst reatures the following disadvantages, namely: rapid deactivation of the catalyst with no opportunity for subsequent regeneration thereof; impossibility to obtain butene-1 at a high yield by dimerization of ethylene (obtained are mainly cis- and transbutene-2 with the content of up to 98%); impossibility to obtain methylpentenes at a high yield by dimerization of propylene (obtained is mainly 2,3-dimethylbutene-2 with the content of up to 80%).

It is an object of the present invention to provide a method for dimerization of olefins having 2 to 4 carbon atoms of from 2 to 4 which would enable the production of butene-1 and methylpentenes at a high yield.

It is another object of the present invention to provide a method for dimerization of olefins containing 2 to 4 carbon atoms which would make use of a catalyst possessing a high stability and capable of being regenerated.

These and other objects of the present invention are accomplished by a process, wherein at least one of said olefins is mixed, in a medium of hydrocarbon or halogenated hydrocarbon solvents at a temperature ranging from 0° to 100° C. under a pressure of from 1 to 40 atm, with a two-component catalyst consisting of:

(1) a complex of a nickel salt of an organic or inorganic acid with tertiary phosphine or tertiary phosphite, and (2) an organoaluminum compound comprising natural or synthetic carbo-chain rubber, swellable in said solvents, containing 2 to 50 mol.% of —AlRX—units, wherein R is an alkyl with at most 8 carbon atoms; X is a halogen; atomic ratio Al/Ni being varied from 1:1 to 100:1.

The catalyst employed in the present invention comprises a gel swellable but insoluble in the reaction medium and permeable, over its entire volume, for both the starting olefin and the reaction products. Said gel-like catalyst can be used in the process for a long period without losing its initial activity; it is not disintegrated during the process and readily regenerated.

The catalyst features high selectivity: as a result of ethylene dimerization butene-1 is produced at a high yield (the content of butene-1 in the resulting mixture of butenes is as high as 80%); dimerization of propylene results mainly in methylpentenes (the content of methylpentenes in the resulting dimerizate is as high as 90–95%).

The process for dimerization of olefins containing 2 to 4 carbon atoms according to the present invention comprises mixing at least one of said olefins with a catalyst in a medium of hydrocarbon solvents (aliphatic, aromatic hydrocarbons) or halogenated hydrocarbon solvents at a temperature ranging from 0° to 140° C., preferably from 10° to 50° C., under a pressure of from 1 to 40 atm, preferably from 1 to 10 atm, in batch-type reactors (under stirring) or in continuous-flow tubular reactors. In the dimerization method according to the present invention use is made of both individual olefins (ethylene, propylene, butene) and mixtures thereof (e.g. a mixture of ethylene with propylene).

As it has been mentioned hereinabove, the catalyst of the present invention is made of a two-component catalyst consisting of (1) a complex of a nickel salt of an organic or inorganic acid with a tertiary phosphine or tertiary phosphite, and (2) an organoaluminum compound comprising natural or synthetic carbo-chain rubber swellable in said solvents and containing 2 to 50 mol.% of —AlRX— units, wherein R is an alkyl containing at most 8 carbon atoms, X is a halogen; atomic ratio Al/Ni is varied within the range of from 1:1 to 100:1, preferably from 5:1 to 10:1.

To prepare said catalyst, as the nickel salt of an organic or inorganic acid use is made, for example, of nickel acetylacetonate, nickel oleate, nickel dichloride.

As tertiary phosphines use is made, for example, of triphenylphosphine, tri-n-octylphosphine, tricyclohexylphosphine triisopropylphosphine.

As tertiary phosphites use is made, for example, of triphenylphosphite, triisopropylphosphite, tri-n-butylphosphite.

Said complex of a nickel salt with a tertiary phosphine or tertiary phosphite is prepared by a conventional method comprising mixing an appropriate salt of nickel with a corresponding tertiary phosphine or tertiary phosphite in a solvent such as benzene, methanol, diethyl ether and the like, at a temperature of from 20° to 30° C.

To prepare the second component of the catalyst (i.e. organoaluminum compound) use is made of both natural and synthetic carbo-chain rubber such as cis- and trans-polybutadiene, isoprene rubber, ternary copolymers of ethylene, propylene and a non-conjugated diene, preferable graft-copolymers of said rubber with 1,2-polybutadiene.

The rubber is pre-reticulated by means of peroxide initiators such as benzoyl peroxide. The resulting cross-linked rubber features a swellability in hydrocarbon solvents and halogenated hydrocarbons.

Preparation of the second catalyst component is effected in a medium of hydrocarbon solvents by reacting said rubber with dialkylaluminum hydride, preferably diisobutyl-aluminum hydride, at a temperature ranging from 0° to 100° C. or with trialkylaluminum, preferably triisobutylaluminum, at a temperature ranging from 100° to 160° C. Amount of dialkylaluminum hydride or trialkylaluminum relative to the rubber chain unit is within the range of from 2 to 50 mol.%. The resulting product in said medium of solvents is subjected to interaction with the stoichiometric amount (relative to the content of aluminum in rubber) of chlorine or aluminum halide, preferably aluminum chloride, or alkylaluminum dihalide, preferably ethylaluminum dichloride or isobutylaluminum-dichloride, or with an excess (at least 10-fold of the stoichiometric amount) of dialkylaluminumhalide, preferably diisobutylaluminumchloride, at a temperature ranging from 20° to 50° C.

The second component, prepared in the manner described hereinabove, is mixed with the previously prepared complex of nickel salt in a medium of hydrocarbon or halogenated hydrocarbon solvents and maintained at a temperature ranging from 0° to 50° C. for a period of from 1 to 24 hours. Thereafter, the resulting gellike catalyst is thoroughly washed with the solvent to remove possible traces of non-reacted low-molecular organometallic compounds.

The catalyst employed in the process according to the present invention is used in the form of granules swollen in said solvents having a size of from 0.1 to 5 mm. These granules are readily permeable, over the entire volume thereof, for molecules of the reagents and the resulting reaction products.

For a better understanding of the present invention the following specific Examples illustrating dimerization of olefins are given hereinbelow.

EXAMPLE 1

Into a 50 ml reactor provided with a stirrer there is charged 0.25 g of granules of cross-linked ternary copolymer of ethylene, propylene and vinylnorbornene containing 10 mol.% of double bonds and 15 ml of absolute heptane. Then 1.8 ml of a 0.5 M solution of diisobutylaluminumhydride in absolute heptane is added into the reactor under vacuum. The resulting mixture is kept at a temperature of 50° C. for 10 hours. Further, 1.8 ml of a 0.5 M solution of ethylaluminum dichloride in absolute heptane is added into the reactor and a mixture is kept at the temperature of 50° C. for additional 2 hours. Thereafter, rubber granules containing 10 mol.% of Al(iso-Bu)-Cl units are thoroughly washed with absolute heptane to remove low-molecular organoaluminum compounds. Then 5 ml of a benzene solution of a complex formed from 0.047 g of nickel acetylacetonate and 0.097 g of triphenylphosphine are added into the reactor. The reaction mixture is left to stay for 10 hours at the temperature of 20° C. Afterwards, the catalyst granules (atomic ratio Al/Ni is 5) are thoroughly washed with absolute heptane (swelling degree of the catalyst is as follows: 0.1 g of the catalyst absorbs 0.9 ml of heptane at the temperature of 20° C.), and then ethylene is fed into the reactor at the temperature of 20° C. under the pressure of 2.5 atm. After a period of one hour the reaction is stopped. The dimerization products are distilled-off and collected into a alceiver. Composition of butenes (as determined by gas-liquid chromatography): 80% of butene-1, 9% of cis-butene-2 and 11% of trans-butene-2.

EXAMPLE 2

Into a 50 ml reactor provided with a stirrer and containing granules of cross-linked rubber with 10 mol.% of —Al(isoBu)—Cl units (this rubber is produced in a manner similar to that of Example 1 hereinabove) a complex of nickel chloride and triphenylphosphine (molar ratio of P/Ni is 2) in 15 ml of absolute cyclohexane is added. The reaction mixture is stirred at the temperature of 20° C. for 10 hours, whereafter the catalyst granules are thoroughly washed with cyclohexane. Then, into the reactor containing the thus-prepared catalyst (atomic ratio Al/Ni is 8) and 15 ml of absolute cyclohexane, propylene is fed. Dimerization of propylene is conducted at the temperature of 30° C. under the pressure of 1 atm. After a period of one hour the reaction is stopped. The dimerization products are distilled-off and subjected to analysis using gas-liquid choromatography techniques. Obtained is 0.2 g of a mixture of hexenes having the following composition: 7% of 4-methylpentene-1, 13% of cis-4-methylpentene-2, 55%, of trans-4-methylpentene-2, 20% of a mixture of 2-methylpentene-1, cis- and trans- 2-methylpentene-2 and 5% of other hexenes.

EXAMPLE 3

Into a reactor provided with a stirrer there is charged 0.25 g of cross-linked rubber granules prepared by graft-copolymerization of 1,2-polybutadiene with a ternary copolymer of ethylene, propylene and ethylidenenorbornene at the weight ratio between said copolymers of 1:1 and 15 ml of absolute heptane. Then, 5.5 ml of a 0.5 M solution of diisobutylaluminum hydride in absolute heptane are added into the reactor under vacuum. The resulting mixture is maintained for 8 hours at a temperature of 50° C. Thereafter, 5.5 ml of a 0.5 M solution of ethylaluminum dibromide in absolute heptane are added into the reactor and the mixture is maintained for an additional two hours at the temperature of 40° C. The thus-prepared product contains about 30 mol.% of-Al(iso-Bu)Br units. Then, a benzene solution of a complex formed by nickel acetylacetonate and tri-n-octyl-phosphine (molar ratio of P/Ni is 2) is added into a reactor. The mixture is stirred at a temperature of 20° C. for 6 hours. Then the catalyst granules (atomic ratio Al/Ni is about 10) are thoroughly washed with absolute heptane and dried (swelling capacity of the catalyst is the following: 0.1 g of granules absorbs 0.5 ml of chlorobenzene at a temperature of 20° C). Thereafter, into the reactor containing the catalyst 15 ml of chlorobenzene and ethylene are charged. Dimerization of ethylene is conducted at a temperature of 40° C. under the pressure of 5 atm. After a period of one hour the reaction is stopped. As a result, 0.9 g of a mixture of butenes is obtained, having the following composition: 70% of butene-1, 11% of cis-butene-2 and 19% of trans-butene-2.

EXAMPLE 4

Into a reactor provided with a stirrer, there are charged 0.25 g of granules of cross-linked 50%-hydrogenated 1,2-polybutadiene and 15 ml of absolute heptane. Thereafter, 9 ml of a 0.5 M solution of dialuminum hydride in absolute heptane are added into the reactor under vacuum. The resulting mixture is maintained at a temperature of 40° C. for 10 hours. Then 7 ml of a 0.5 M solution of ethylaluminum dichloride in absolute heptane are added into the reactor and maintained for an additional two hours at a temperature of 50° C. Thereafter, the rubber granules containing about 40 mol.% of —AlEtCl units are thoroughly washed with absolute heptane to remove low-molecular organoaluminum compounds and then mixed with a complex of nickel acetylacetonate and triphenylphosphite under the conditions of Example 1. A catalyst is thus obtained, with the atomic ratio of Al/Ni of about 19; swelling capacity of the catalyst is the following: 0.1 g of granules absorbs 0.35 ml of heptane at 20° C. Then, 15 ml of absolute decane are introduced into the reactor and ethylene is fed thereinto. Dimerization of ethylene is conducted at 100° C. under a pressure of 40 atm. After a period of one hour the reaction is stopped to give a mixture of butenes having the following composition: 80% of butene-1, 7% of cis-butene-2 and 13% of trans-butene-2.

EXAMPLE 5

Into a reactor provided with a stirrer and containing 1g of a catalyst similar to that employed in Example 3 hereinabove there are charged 20 ml of butene-1 and ethylene is fed thereinto under a pressure of 2 atm. Dimerization of the resulting mixture of butene-1 and ethylene is conducted at 0° C. After a period of one hour the reaction products are distilled-off and analysed. There is obtained 0.3 g of a mixture of hexenes, consisting of 50% of methylpentenes and 50% of linear hexenes.

EXAMPLE 6

Into a reactor provided with a stirrer there are charged 0.5 g of cross-linked, 1,2-polybutadiene containing 90 mol.% of vinyl groups and 15 ml of absolute heptane. Then, in the absence of air and humidity there are added 10 ml of a 0.5 M solution of diisobutylaluminum hydride in absolute heptane. The resulting mixture is maintained at 50° C. for 10 hours. Afterwards, added into the reactor are 10 ml of a 0.5 M solution of ethylaluminum dichloride in absolute heptane and the mixture is maintained for additional two hours at 50° C. Then the rubber granules containing 50 mol% of Al(iso-Bu)Cl units are thoroughly washed with absolute heptane to remove low-molecular organoaluminum compounds. Thereafter, charged into the reactor are 5 ml of a benzene solution of a complex formed by 0.047 g of nickel acetylacetonate and 0.097 g of triphenylphosphine and the mixture is kept at 20° C. for a period of 10 hours. Further, after thorough washing of the catalyst granules (atomic ratio of Al/Ni is 25) with absolute toluene, ethylene is fed into the reactor. The reaction is conducted at temperature of 10° C. under the pressure of 20 atm. in the medium of toluene. After a period of one hour the reaction is stopped to give 2.4 g of a mixture of butenes of the following composition: 82% of butene-1, 9% of cis-butene-2 and 9% of trans-butene-2.

EXAMPLE 7

Dimerization of ethylene is conducted in the medium of n-octylbromide in presence of a catalyst similar to that employed in Example 6 hereinbove (atomic ratio Al/Ni is 100) at 50° C. under a pressure of 10 atm. There is obtained a mixture of butenes of the following composition: 75% of butene-1, 12% of cis-butene-2 and 13% of trans-butene-2.

EXAMPLE 8

Into a reactor provided with a stirrer there are charged 0.5 g of granules of cross-linked 50% hydrogenated 1,2-polybutadiene and 15 ml of absolute heptane. Thereafter, 5,5 ml of a 0.5 M solution of triisobutylaluminum in absolute heptane are added into the reactor under vacuum. The resulting mixture is maintained at 100° C. for 10 hours. Then, 5.5 ml of a 0.5 M solution of ethylaluminum dichloride in absolute heptane are introduced into the reactor and the resulting mixture is maintained for additional 2 hours at 50° C. Afterwards, the rubber granules containing 27 mol.% of Al(iso-Bu)Cl units are thoroughly washed with absolute heptane to remove low-molecular organoaluminum compounds, whereafter they are mixed, under the conditions of the foregoing Example 1, with a complex of nickel dicromide and triphenylphosphine. In the catalyst thus prepared the ratio of Al to Ni is 1. Into a reactor containing the resulting catalyst, ethylene is fed and the reaction is conducted at 70° C. under a pressure of 6 atm in a medium of absolute heptane. After 2 hours the reaction is stopped to give a mixture of butenes containing: 80% of butene-1, 8% of cis-butene-2 and 12% of trans-butene-2.

EXAMPLE 9

Into a reactor provided with a stirrer there are charged 1 g of granules of cross-linked 1,4-cis-polybutadiene (the content of cirs-units is about 85%) and 25 ml of absolute heptane. Thereafter, 1 ml of a 0.5 M solution of ethylaluminum dibromide in absolute heptane is added into the reactor and the mixture is maintained at a temperature of 50° C. for 8 hours. Then 1.5 ml of a 0.5 M solution of ethylaluminum dibromide in absolute heptane is introduced into the reactor and the mixture is maintained for an additional 3 hours 50° C. Afterwards the rubber granules containing about 2 mol.% of Al(iso Bu)Br units are thoroughly washed with absolute heptane to remove low-molecular organoaluminum compounds and then mixed, under the conditions of the foregoing Example 1, with a complex of nickel acetylacetonate and triphenylphosphine, the result being a catalyst with the atomic ratio Al/Ni of 6. Dimerization of ethylene is conducted in the medium of absolute heptane at 250° C. under a pressure of 4 atm. After a period of 4 hours the reaction is stopped and 0.6 g of butenes is collected in a receiver. The mixture of butenes has the following composition: 81% of butene-1, 6% of cis-butene-2 and 13% of trans-butene-2.

EXAMPLE 10

Into a reactor provided with a stirrer there are charged 1 g of cross-linked graft copolymer of natural rubber with 1,2-polybutadiene (weight ratio between the rubbers is 8:2 respectively) containing about 15 mol.% of Al(n-octyl)-Cl units (prepared by the procedure of Example 3 hereinbefore using, instead of diisobutylaluminum hydride, dioctylaluminum hydride, at 100° C.), 25 ml of absolute heptane and a benzene solution of a complex of nickel acetylacetonate and triphenylphosphine. After washing the resulting catalyst granules with absolute heptane to remove low-molecular organometallic compound, a catalyst is obtained, having atomic ratio Al/Ni equal to 6. Thereafter, ethylene fed into the reactor and dimerization is conducted in the medium of absolute heptane at 20° C. under a pressure of 2.5 atm.

A mixture of butenes is obtained having the following composition: 81% of butene-1, 7% of cis-butene-2 and 12% of trans-butene-2.

EXAMPLE 11

Into a reactor provided with a stirrer, containing 0.5 g of the catalyst granules similar to those of Example 2 herein-before (atomic ratio of Al/Ni is 10) and 20 ml of absolute heptane are charged, whereafter propylene is fed into the reactor. The dimerization reaction is conducted at 30° C. under a pressure of 6 atm. After every 6 hours the dimerization products are distilled-off to leave, in the reactor, the amount of liquid equal to the volume of liquid at the beginning of the experiment, whereafter propylene is again fed into the reactor.

The above-mentioned operations are successively repeated 8 times. Total dimerization time is 48 hours. During the entire experiment the dimerization rate and composition of products remained, on the average, constant.

What is claimed is:

1. In a dimerization catalyst consisting of a complex of a nickel salt with a compound selected from the group consisting of tertiary phosphines and tertiary phosphites in combination with an organoaluminum compound wherein the improvement comprises using as the organoaluminum compound a rubber selected from the group consisting of natural and synthetic carbo-chain rubber with a content of 2 to 50 mol% of AlRX units, wherein R is an alkyl with at most 8 carbon atoms, X is a halogen; the atomic ratio of Al/Ni being varied within the range of from 1:1 to 100:1.

2. The dimerization catalyst of claim 1, consisting of:
   (a) a complex of nickel acetylacetonate with triphenylphosphine; and
   (b) a graft-copolymer of 1,2-polybutadiene with a rubber selected frm the group consisting of natural rubber, 1,4-cis-polybutadiene and a ternary copolymer of ethylene, propylene and ethylidenenorbornene; said graft-copolymer containing 2 to 50 mol.% of AlRX units, wherein R is isobutyl, X is chlorine: atomic ratio Al/Ni being varied between the range of from 5:1 to 10:1.

3. The dimerization catalyst of claim 1, wherein the atomic ratio of Al/Ni varies from 5:1 to 10:1.

* * * * *